United States Patent
Chung et al.

(10) Patent No.: US 9,404,116 B2
(45) Date of Patent: Aug. 2, 2016

(54) METHOD OF CONSTRUCTION OF RECOMBINANT ORGANISMS USING MULTIPLE GENES CO-INTEGRATION

(71) Applicant: Samsung Electronics Co., Ltd., Suwon-si, Gyeonggi-do (KR)

(72) Inventors: Soon-chun Chung, Seoul (KR); Hyun-min Koo, Seoul (KR); Ji-eun Kim, Seoul (KR); Jae-chan Park, Yongin-si (KR); Joon-song Park, Seoul (KR); Ju-young Lee, Daegu (KR)

(73) Assignee: SAMSUNG ELECTRONICS CO., LTD., Suwon-Si (KR)

( * ) Notice: Subject to any disclaimer, the term of this patent is extended or adjusted under 35 U.S.C. 154(b) by 0 days.

(21) Appl. No.: 14/198,124

(22) Filed: Mar. 5, 2014

(65) Prior Publication Data
US 2014/0256045 A1   Sep. 11, 2014

(30) Foreign Application Priority Data

Mar. 5, 2013   (KR) .................. 10-2013-0023575

(51) Int. Cl.
*A01N 63/00* (2006.01)
*C12N 15/80* (2006.01)
*C12N 15/81* (2006.01)

(52) U.S. Cl.
CPC ............... *C12N 15/80* (2013.01); *C12N 15/81* (2013.01); *C12N 15/815* (2013.01)

(58) Field of Classification Search
CPC ....... C12N 15/80; C12N 15/81; C12N 15/815
USPC ...................... 435/254.1, 325, 471
See application file for complete search history.

(56) References Cited

U.S. PATENT DOCUMENTS

| | | | |
|---|---|---|---|
| 8,685,737 B2 * | 4/2014 | Serber et al. | 435/471 |
| 8,778,641 B1 * | 7/2014 | Spodsberg | 435/99 |
| 2004/0126883 A1 | 7/2004 | Liu | |
| 2004/0214222 A1 | 10/2004 | Burgess, Jr. et al. | |
| 2009/0317910 A1 | 12/2009 | Church et al. | |
| 2011/0020889 A1 | 1/2011 | Feldman et al. | |
| 2011/0053219 A1 | 3/2011 | Nicaud et al. | |
| 2011/0275541 A1 | 11/2011 | Cheo et al. | |

FOREIGN PATENT DOCUMENTS

EP   0575338 A1   6/1992

OTHER PUBLICATIONS

Nonklang et al. Applied Environ Microbiol 2008;74:7514-21.*
Abdel-Banat et al. Yeast 2010;27:29-39.*
Fang et al. Yeast 2011;28:123-36.*
Valencia et al. Nat 2001; 414:666-9.*
Peredelchuk et al. A method for construction of *E. coli* strains with multiple DNA insertions in the chromosome, *Gene*, 187: 231-238 (1997).
Haldimann et al., Conditional-Replication, Integration, Excision, and Retrieval Plasmid-Host Systems for Gene Structure-Function Studies of Bacteria, *Journal of Bacteriology*, 183(21): 6384-6393 (2001).
Cavaliere et al., Testing for co-integration in vector autoregressions with non-stationary volatility, *School of Economics and Granger Centre for Time Series Econometrics, Univ. of Nottingham*, Granger Centre Discussion Paper Series No. 07/02 (Aug. 2007).
Bartkeviciute et al., "Heterologous expression of the Kluyveromyces marxianus endopolygalacturonase gene (EPG1) using versatile autonomously replicating vector for a wide range of host", *Enzyme and Microbial Technology*, 26: 653-656 (2000).
Kimura et al., "Production of HM-1 Killer Toxin in *Saccharomyces cerevisiae* Transformed with the PDR4 Gene and δ-Sequence-Mediated Multi-Integration System", *Journal of Fermentation and Bioengineering*, 80:(5), 423-428 (1995).
Koma et al., A convenient method for multiple insertions of desired genes into target loci on the *Escherichia coli* chromosome, *Appl Microbiol Biotechnol*, 93:815-829 (2012).
Albermann et al. "A simple and reliable method to conduct and monitor expression cassette integration into the *Escherichia coli* chromosome", *Biotechnology Journal*, 5, 32-38 (2010).
Siekstele et al., Cloning, Targeted Disruption and Heterologous Expression of the *Kluyveromyces marxianus* Endopolygalacturonese Gene (EPG1), *Yeast*, 15, 311-322 (1999).
Ohgiya et al., Establishment of a Novel Host, High-Red Yeast That Stably Expresses Hamster NADPH-Cytochrome P450 Oxidoreductase: Usefulness for Examination of the Function of Mammalian Cytochrome P450, *Archives of Biochemistry and Biophysics*, 343(2), 215-224 (1997).
Li et al., "Multiple inserts of gene of interest and selectabie marker gene are co-integrated and stably transmitted as a single genetic locus in transgenic soybean plants", *In Vitro Cell. Dev. Biol.-Plant*, 47:274-281 (2011).
Ikawa et al, Generation of Transgenic Mice Using Lentiviral Vectors: A Novel Preclinical Assessment of Lentiviral Vectors for Gene Therapy, *Molecular Therapy*, 8(4), 666-673 (2003).

* cited by examiner

*Primary Examiner* — Janice Li
(74) *Attorney, Agent, or Firm* — Leydig, Voit & Mayer, Ltd.

(57) ABSTRACT

Provided is a method of simultaneous co-integration of multiple nucleic acid sequences into a microbial organism comprising culturing a microbial organism to be transformed until a growth phase is reached in which a random integration is facilitated; and transforming the microbial organism by mixing the cultured microbial organism with a sample to be co-integrated into the microbial organism with, wherein the sample comprises more than one nucleic acid sequence, and the products generated from the method.

8 Claims, 4 Drawing Sheets

METHOD OF CONSTRUCTION OF RECOMBINANT ORGANISMS USING MULTIPLE GENES CO-INTEGRATION

CROSS-REFERENCE TO RELATED APPLICATION

This application claims the benefit of Korean Patent Application No. 10-2013-0023575, filed on Mar. 5, 2013 in the Korean Intellectual Property Office, the entire disclosure of which is hereby incorporated by reference.

INCORPORATION-BY-REFERENCE OF MATERIAL ELECTRONICALLY SUBMITTED

Incorporated by reference in its entirety herein is a computer-readable nucleotide/amino acid sequence listing submitted herewith and identified as follows: One 38,086 bytes ASCII (Text) file named "716221_ST25.TXT," created on Mar. 3, 2014.

BACKGROUND OF THE INVENTION

1. Field

The present disclosure relates to methods of simultaneously transforming various types of nucleic acid sequences (e.g., genes) efficiently.

2. Description of the Related Art

Much biomaterials research is currently underway. Specifically, research into the production of industrially useful materials using microbes (i.e., microbial organisms) is in progress. However, microbial organisms do not only produce desired metabolites. When specific metabolites are produced in excess, growth of the microbial organisms may be inhibited, and the microbial organisms may no longer produce the desired metabolites or may produce undesirable by-products.

To overcome such limitations, research is underway to develop microbial organisms that may uniquely produce the desired metabolites. However, preparing transformed microbial organisms by transforming all metabolic pathways of the microbial organism requires a long period of time and great effort.

Specifically, the greater the number of nucleic acid sequences to be transformed, the greater the number of processes that are needed during the transformation. Each process is laborious and requires a long period of time, and gene transfer efficiency decreases. Accordingly, there is a need for improvement in gene transfer methods.

Microbial growth occurs regularly for a certain period of time, during which the microbes grow exponentially. However, after a certain period of exponential growth, the microbes show a slowed growth rate. When a population of the microbes is shown as a function of time, a typical S shaped curve may be obtained. A graph illustrating a number of the microbe population as a function of time is referred to as a growth curve of the microbes. The growth curve may be divided into four phases.

The first phase is a lag phase. The lag phase is a period in which the microbes adjust to a new medium. When the microbes are inoculated and cultured in the new medium, chemical changes such as an activation of enzymes and an increase in cell components such as RNAs occur. During the lag phase, the amount of RNA in cells increases substantially, the size of the microbes increases and respiratory activity of the microbes is high.

The second phase is a log phase. During the log phase, the microbes that passed through the lag phase grow actively. The log phase is a period in which the microbes grow logarithmically. As physiological functions of the microbes increase during the log phase, the microbes begin to excrete enzymes and become sensitive to physical and chemical treatments. Also, generation time and the size of the microbes are uniform during the log phase and the growth rate is determined according to environmental factors such as nutritive conditions, pH, temperature, and oxygen partial pressure of the medium.

The third phase is a stationary phase. The number of the microbes becomes constant after the log phase, the highest number of the microbes is maintained, and the microbes excrete enzymes, during this phase. Also during the stationary phase, some cells die while others grow, thereby maintaining a constant state where a number of dying microbes and a number of proliferating microbes are almost the same. Also, as the overcrowding of microbes causes depletion of nutrients, accumulation of metabolites of the microbes, changes in pH of the medium, and a depletion of the oxygen supply, the environment becomes unsuitable for growth of the microbes, and thus, the number of the microbes does not increase.

The last phase is a death phase. This is the final phase of culturing where the number of the microbes decreases. The primary reasons for death include dissolution of cells due to a decomposition caused by nuclease or protease, denaturing of enzymatic proteins, and autolysis of microbes killed by enzymes.

The microbes may be transformed by using microbes in an initial phase of the log phase, which is a period when the cells are most active and $OD_{600}$ value is between about 0.5 to about 1.0. When the microbes subject to the transformation and the conditions of the transformation are controlled, an increase in the efficiency of the transformation may be observed.

BRIEF SUMMARY OF THE INVENTION

Provided are methods of efficiently preparing genetically recombined microbes (i.e. microbial organisms) by simultaneously co-integrating multiple nucleic acid sequences (e.g., genes) into a microbial organism.

Additional aspects will be set forth in part in the description which follows and, in part, will be apparent from the description, or may be learned by practice of the presented embodiments.

BRIEF DESCRIPTION OF THE DRAWINGS

These and/or other aspects will become apparent and more readily appreciated from the following description of the embodiments, taken in conjunction with the accompanying drawings of which:

FIG. 1A illustrates a method of transformation by using a sequential gene integration. FIG. 1B illustrates a method of transformation by using a multiple gene expression vector. FIG. 1C illustrates a method of transformation by using co-transformation of multiple vectors;

DETAILED DESCRIPTION OF THE INVENTION

Figure 1A:
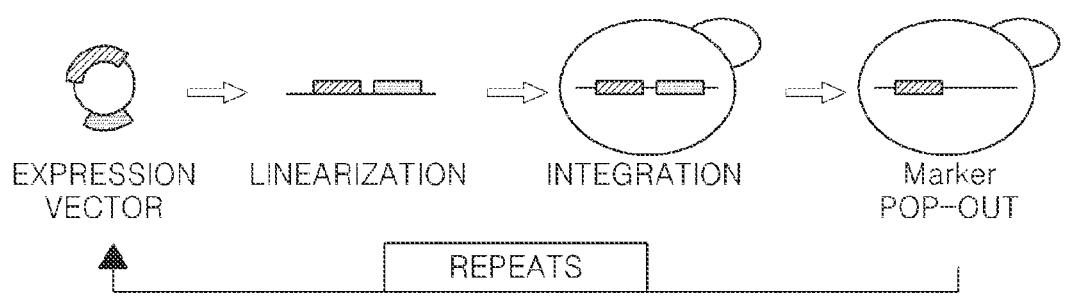
FIGS. 1A to 1C illustrate a system for preparing a recombinant strain, respectively.

According to an aspect of the present disclosure, there is provided a method for the simultaneous co-integration of multiple nucleic acid sequences including culturing a microbial organism to be transformed until a phase in which a random integration is initiated; and transforming the microbial organism by mixing the cultured organism with a sample to be co-integrated into the microbial organism, wherein the sample comprises more than one nucleic acid sequence.

A method for the simultaneous co-integration of multiple nucleic acid sequences is as follows.

First, the method includes culturing a microbial organism to be transformed until a growth phase is reached in which a random integration is facilitated. Here, the phase in which the random integration is facilitated may vary depending on the microbial organism cultured.

An embodiment of the phase in which the random integration is facilitated may be in a state where the microbial organism has a cell density greater than its cell density during its log phase of growth. Here, the state in which the cell density is greater than the cell density of the log phase may have an optical density at 600 nm ($OD_{600}$) of about 2.0 to about 10.0. Also, the $OD_{600}$ may be about 3.5 to about 8.0. Also, the $OD_{600}$ may be about 3.5 to about 6.0, and may be about 4.0 to about 5.0. However, if the $OD_{600}$ is a value selected from the latter half of the log phase, or from a stationary phase, the $OD_{600}$ in a flask may be suitably selected between 3.0 and 8.0. Also, the $OD_{600}$ may be suitably selected according to the chosen type of microbial organism.

The microbes to be transformed may be a strain having a non-homologous end joining (NHEJ) as a dominant system. The term "a non-homologous end joining as a dominant system" means that NHEJ is more dominant than homologous recombination as DNA repair system in a microbial organism. Non-homologous end joining (NHEJ) is a pathway that repairs double-strand breaks in DNA. NHEJ is referred to as "non-homologous" because the break ends are directly ligated without the need for a homologous template, in contrast to homologous recombination, which requires a homologous sequence to guide repair. Here, the strain having the NHEJ as a dominant system may be non-conventional yeast, fungi, or mammalian cells. The term "non-conventional yeast" refers to yeast species with outstanding characteristics investigated for biotechnology and research, not to *S. cerevisiae*. The non-conventional yeast may be *Kluyveromyces, Hansenula*, or *Kluyveromyces marxianus*. *K. marxianus* is an acid resistant yeast that may produce organic acids with high efficiency at low acidity and thus, *K. marxianus* may be used as a microbial organism suitable for transformations for industrialization.

Hereinafter, provided is a process for preparing a sample to be co-integrated into the microbes, the sample including more than one nucleic acid sequence.

The sample may contain multiple nucleic acid sequences to be integrated into the microbe. For example, the sample may comprise 2 to 10 different nucleic acid sequences, or 3 to 6 different nucleic acid sequences. However, the sequences may be suitably selected as needed. Also, the nucleic acid sequences may comprise coding sequences for genes of interest. They may also be DNA fragments. As disclosed here, the nucleic acid sequences to be co-integrated may be multiple copies of the same nucleic acid sequence or encoding the same gene product, or different nucleic sequences (e.g., encoding different gene products). Also, the nucleic acid sequences may encode an enzyme participating in a metabolic pathway of the microbial organism, and the nucleic acid sequences may encode a homologous or a heterologous protein expression enzyme. Also, the nucleic acid sequences may be related to a synthesis of organic acids. Also, the nucleic acid sequences may be related to a saccharification.

Also, the nucleic acid sequences to be included in the sample may be linear genes obtained by inserting the genes into vectors and excising an autonomously replicating sequence (ARS) in the vectors by a restriction enzyme. The restriction enzyme removes the ARS sequence existing in the vector, and enables the ARS sequence to be used as a linear gene. The types of the restriction enzyme used may vary depending on the genes to be co-integrated. The restriction enzyme may be PfoI, HindIII, XhoI, BgIII, KpnI, PacI, and/or AatII; however, the restriction enzyme is not limited thereto.

The term "vector" as used herein refers to a DNA product including a DNA sequence operably linked to a suitable regulatory sequence for expressing DNA in a suitable host. Vectors such as a plasmid vector, a bacteriophage vector, or a cosmid vector, and preferably the plasmid vector may be used. Also, the nucleic acid sequences may be connected to an operable promoter.

Thereafter, provided is a phase for mixing the prepared sample and the cultured microbial organism, thereby transforming the microbial organism.

Here, the transformation process may involve the simultaneous co-integration of multiple nucleic acid sequences. This involves a simultaneous co-integration of multiple nucleic acid sequences into a microbial organism during one co-integration process by using an NHEJ system. Such a process is referred to as multiple genes co-integration technology.

Figure 1B:
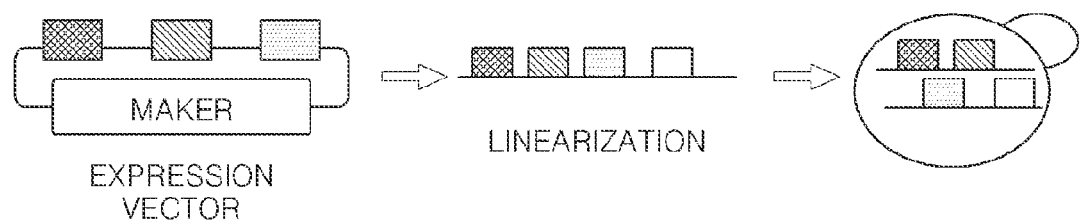
Figure 1C:
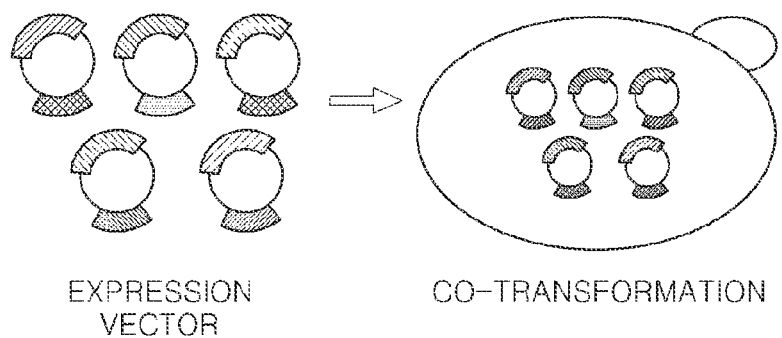
Figure 2:
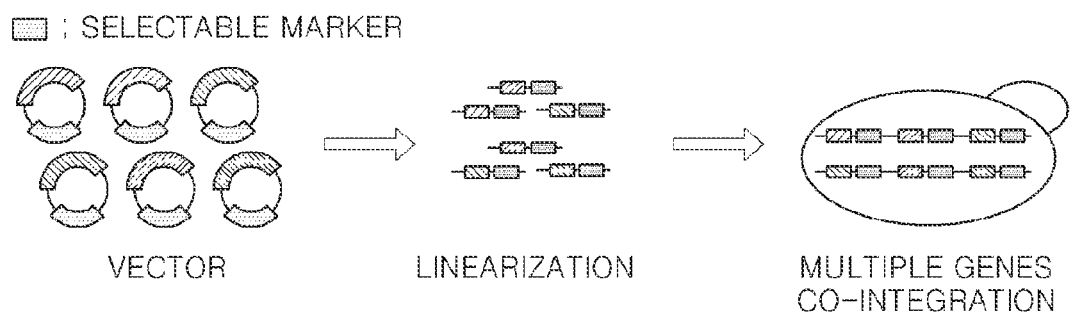
FIG. 2 illustrates a summary of simultaneous co-integration of multiple nucleic acid sequences (e.g., genes) using a non-homologous end joining (NHEJ) system.

Conventionally, co-integrating multiple nucleic acid sequences into a genome of a strain using a multiple co-transformation method requires using plasmids having different selectable markers and the strain must also be manipulated to use the selectable markers. FIGS. 1A to 1C illustrate the conventional system for preparing a recombinant strain, respectively. FIG. 1A illustrates a method of transformation by using a sequential gene integration. FIG. 1B illustrates a method of transformation by using a multiple gene expression vector. FIG. 1C illustrates a method of transformation by using co-transformation of multiple vectors. The conventional method is limited by the number of usable selectable markers.

Figure 4:
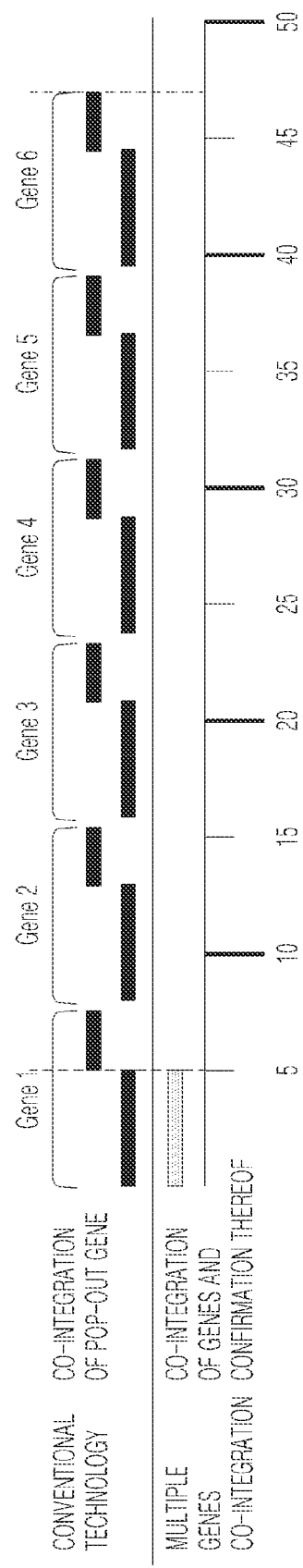
FIG. 4 illustrates a comparison between a sequential transformation method, which is a conventional technology, and a simultaneous co-integration of multiple nucleic acid sequences (i.e., Multiple Genes Co-Integration) according to an embodiment. In the FIG. 4, the labels on the X axis represent day post integration and the horizontal bars represent the period of performing each experiment.

However, the simultaneous co-integration of multiple nucleic acid sequences using the method disclosed herein is not limited by the number of selectable markers. It also takes the same period of time for co-integrating the nucleic acid sequences into the genome regardless of the number of the genes. The period of time for co-integrating the genes into the genome is about 6 days, which is a substantially shortened period of time compared to that of the multiple co-transformation method. Further, the genes may be repeatedly inserted by using a cassette including a repeat sequence where a marker pop-out is possible. The term "marker pop-out" refers to removing or deleting marker gene. FIG. 4 illustrates a comparison between a sequential transformation method, which is a conventional technology, and a simultaneous co-integration of multiple nucleic acid sequences according to an embodiment The simultaneous co-integration of multiple nucleic acid sequences using the method disclosed in the embodiment may use numerous selectable markers. For instance, one to three selectable markers or one selectable marker may be used. The repeat sequence where the marker pop-out is possible may be included.

According to another aspect, there are provided transformed microbial organisms prepared by the method including various types of different genes.

The microbial organisms to be transformed may be a strain having an NHEJ as a dominant system. Here, the strain having the NHEJ as a dominant system may be non-conventional yeast, fungi, or mammalian cells. The non-conventional yeast may be *Kluyveromyces, Hansenula*, and preferably *Kluyveromyces marxianus*. *K. marxianus* is an acid resistant yeast and may be used as the microbial organism for transformation for industrialization, because the yeast may produce organic acids with high efficiency at low acidity.

Also, the nucleic acid sequence may be one or more nucleic acid sequence. Further, the genes may be 2 different or 10 different nucleic acid sequences, and may be 3 different or 6 different nucleic acid sequences. Also, the nucleic acid sequences may encode an enzyme participating in a metabolic pathway of the microbial organism, and the nucleic acid sequences may encode homologous or heterologous protein expression enzymes. Also, the nucleic acid sequences may be related to a synthesis of organic acids. Also, the nucleic acid sequences may be related to a saccharification.

In one embodiment of the present disclosure, there is provided a method for the simultaneous co-integration of multiple nucleic acid sequences including culturing a microbial organism to be transformed until the optical density at 600 nm ($OD_{600}$) is at least about 2.0; and transforming the microbial organisms by mixing the cultured organism with a sample to be co-integrated into them, wherein the sample comprises more than one nucleic acid sequence and the microbial organism has a stronger Non-homologous end joining (NHEJ) than homologous recombination as DNA repair system.

The $OD_{600}$ may be about 2.0 to about 10.0, about 2.5 to about 8.0, about 3.0 to about 8.0, about 3.0 to about 7.0, 3.0 to about 6.5, about 3.0 to about 6.0, about 3.0 to about 5.5 or about 3.0 to about 5.0. The microbial organism to be transformed may be a competent cell. The term "competent cell" refers to a cell which has the ability to take up and replicate an exogenous nucleic acid. In one example, co-integration efficiency of competent cell prepared when $OD_{600}$ was about 3.5 for 6 genes was 100%, while that of competent cell prepared when $OD_{600}$ was about 1.0 was 28%.

Another aspect relates to a method of preparing metabolites by using the transformed microbial organism. The method of preparing the metabolites by using the transformed microbial organism may include culturing the transformed microbial organism; and retrieving the metabolites from a culture medium.

A method of preparing the metabolites is as follows.

First, provided is a process of culturing the transformed microbial organism prepared by the simultaneous co-integration of multiple nucleic acid sequences.

The term "metabolites" as used herein refers to all materials produced by metabolic reactions of the microbial organism. The metabolites may be intermediate products of the metabolic reactions of the microbial organism or final products of the metabolic reactions of the microbial organism. Examples of the metabolites include succinic acid, lactic acid, 1,4-butanediol (1,4-BDO), 3-hydroxypropionate, and the like, but are not limited thereto.

The microbial organism may be cultured in carbon sources usable by the microbial organism such as monosaccharides, disaccharides, or polysaccharides. Specifically, glucose, fructose, mannose, or galactose may be used. Also, nitrogen sources usable by the microbial organism may be organic nitrogen compounds, or inorganic nitrogen compounds. Specifically, the nitrogen sources may be amino acids, amides, amines, nitrates, or ammonium salts. Oxygen conditions for culturing the microbial organism may be an aerobic condition of a normal oxygen partial pressure, a low oxygen condition including about 0.1% to about 10% of oxygen in atmosphere, or an anaerobic condition without oxygen.

Thereafter, provided is a process of retrieving the metabolites from the culture medium.

The metabolites may be succinic acid, 3-hydropropionate (3HP), and lactic acid. The metabolites may be retrieved through, for example, filtering.

Unless defined otherwise, all technical and scientific terms used in the present specification have the same meanings as generally understood by one of ordinary skill in the art. Generally, nomenclatures used in the present specification are well known and commonly used in the art.

Reference will now be made in detail to embodiments. The following embodiments are for illustrative purposes only and it is apparent to one of ordinary skill in the art that the scope of the present invention is not limited by the embodiments. Specifically, the embodiments only show a method using *K. marxianus* as a model system; however, it is apparent to one of ordinary skill in the art that the embodiments also apply to other microbial organism than *K. marxianus* based on the present specification.

EXAMPLE 1

Preparing a Gene Expression Vector

Figure 3:
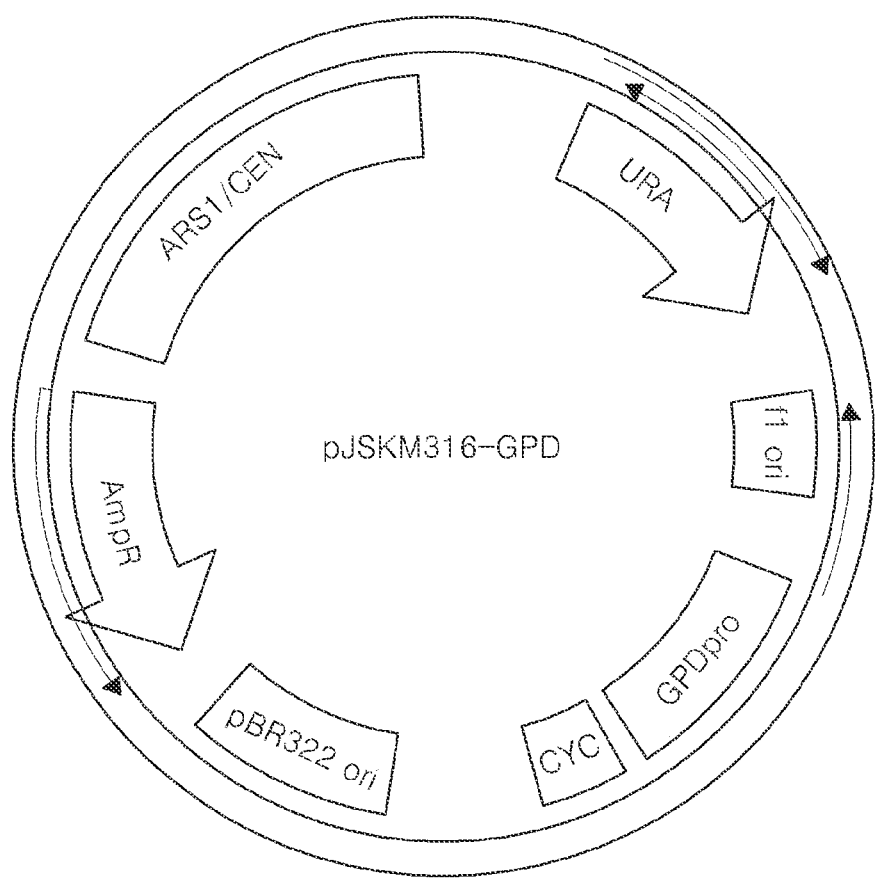
FIG. 3 illustrates an expression vector for expressing nucleic acid sequences within *K. marxianus*.

To prepare a gene expression vector that may be co-integrated into a uracil (Ura) auxotrophic *K. marxianus* strain, a replication origin, an autonomously replicating sequence (ARS), and a centromere of *K. marxianus* were amplified by a polymerase chain reaction (PCR) to prepare amplified products, and the amplified products were co-inserted into a pRS306 vector purchased from ATCC to prepare a *K. marxianus-E. coli* shuttle vector. A GPD promoter and a CYC terminator gene were inserted into the shuttle vector (pJSKM316-GPD, SEQ No. 1; FIG. 3). *Sacharomyces cerevisiae* ALD6 (SEQ No. 2), *S. cerevisiae* ACS2 (SEQ No. 3), and *K. marxianus* ACC (SEQ No. 4) genes were enabled to be expressed in *K. marxianus* by the GPD promoter and the CYC terminator. FIG. 3 illustrates an expression vector for expressing nucleic acid sequences within *K. marxianus*.

EXAMPLE 2

Co-Integrating Genes into *K. marxianus*

2-1. Preparing Competent Cells by Using *K. marxianus* Strain

The Ura auxotrophic *K. marxianus* strain was streaked in a Glycerol stock on a YPD plate and cultured at a temperature of 37° C. for 2 days. One colony was inoculated in 100 ml of YPD culture medium, and cultured at a temperature of 37° C. at 250 rpm overnight. The colony was cultured until $OD_{600}$ reached about 3.0 to about 5.0, and the same was centrifuged at 5,000 rpm for 5 minutes to separate cells. After washing the cells with 60 ml of sterilized water, 10 ml of lithium acetate buffer (100 mM lithium acetate, 10 mM Tris-Cl pH 7.5, 10 mM DTT, and 0.6M Sorbitol) was added thereto, and the cells were maintained at room temperature for 30 minutes. Thereafter, the cells were washed three times by using 10 ml of 1M sorbitol, and resuspended by using 1 ml of 1M sorbitol, divided the cells into 100 ul, and maintained the cells at a temperature of −80° C. and used.

2-2. Preparing DNA Sample for Transformation pJSKM316-GPD_inBGL1 (intracellular beta-glucosidase), pJSKM316-GPD_exBGL1 (extracellular beta-glucosidase), pJSKM316-GPD_EG1 (endoglucanase), pJSKM316-GPD_CBH1 (cellobiohydrolase), and pJSKM316-GPD_CBH2 (cellobiohydrolase II) plasmids were individually treated with PacI restriction enzyme respectively to excise ARS1/CEN from the plasmid, and then electrophoresed in an agarose gel. Linear DNA fragments other than 800 bps of ARS were each extracted from the agarose gel.

2-3. Multiple Co-Integration of Various Genes in *K. marxianus* Strain 300 ng of each linear DNA fragment were transformed into the *K. marxianus* competent cells (such that the total DNA volume is less than 10 ul) by combining the linear DNA fragments with the cells. Thereafter, the *K. marxianus* competent cells were reacted in ice for 20 minutes and then electroporated (MicroPulser Electorporator, available from Bio-Rad). Thereafter, the *K. marxianus* competent cells were resuspended by using 1 ml of YPDS (YPD+1M sorbitol) and cultured at a temperature of 37° C. for 2 hours at 250 rpm, spread on synthethic media (6.7 g/L Yeast nitrogen base w/o amino acid, 1.92 g/L Synthetic drop-out mix w/o uracil, 20 g/L glucose, and 20 g/L agar), and cultured at a temperature of 37° C. for 36 hours.

2-4. Confirming Genes Co-Integrated Into *K. marxianus* Strain

After co-integrating the genes, the *K. marxianus* competent cells were spread on minimal media having no uridine and cultured at a temperature of 37° C. for 2 days. After extracting genomic DNA from a single colony, gene co-integration was confirmed through PCR, and *K. marxianus* strain where all of ALD6, ACS1, and ACC genes were co-integrated was obtained. To amplify each gene, primers of Table 1 were used. Also, a PCR process involved treating the *K. marxianus* competent cells for 2 minutes at a temperature of 95° C., and then repeating for 30 times a thermal denaturation for 30 seconds at a temperature of 95° C., an annealing for 30 seconds at a temperature of 55° C., and an elongation for 3 minutes at a temperature of 72° C. to prepare a reaction product, and the reaction product was reacted for 54 minutes at a temperature of 72° C.

TABLE 1

| Amplified materials | | Sequences | SEQ No. |
|---|---|---|---|
| ALD6 | Forward-direction primer | 5'-cattatcaatactcgccatttcaaag-3' | SEQ No. 5 |
| | Reverse-direction primer | 5'-ttacaacttaattctgacagcttttac-3' | SEQ No. 6 |
| ACS2 | Forward-direction primer | 5'-cattatcaatactcgccatttcaaag-3' | SEQ No. 7 |
| | Reverse-direction primer | 5'-ttatttcttttgttggttaagaattggg-3' | SEQ No. 8 |
| ACC | Forward-direction primer | 5'-cattatcaatactcgccatttcaaag-3' | SEQ No. 9 |
| | Reverse-direction primer | 5'-tcattccaaagccttttgaagcttttctttg-3' | SEQ No. 10 |

EXAMPLE 3

Co-Integration Efficiency According to OD Values of Strains

As shown in Example 2, dhaB1 (SEQ No. 11), dhaB2 (SEQ No. 12), dhaB3 (SEQ No. 13), gdrA (SEQ No. 14), gdrB (SEQ No. 15), aldH (SEQ No. 16), and KGSadh (SEQ No. 17) were inserted into a vector, respectively, and the vectors were excised by using a restriction enzyme to prepare a sample including the genes for transformation. Thereafter, the genes were co-integrated into *K. marxianus* competent cells. Also, primers in Table 2 were used to confirm the co-integration of the genes. Table 3 shows the co-integration efficiency and strain preparation time of *K. marxianus* when $OD_{600}$ is 1 (Exp.1) and 3.5 (Exp.2). Specifically, Exp. 1 is relates to competent cell cultured until an optical density of 600 nm ($OD_{600}$) of the cell is 1 and Exp. 2 is relates to competent cell cultured until an $OD_{600}$ of the cell is 3.5.

TABLE 2

| Amplified materials | | Sequences | SEQ No. |
|---|---|---|---|
| dhaB1 | Forward-direction primer | 5'-ATT GTG GAG TTG GAT GGT AAG CGT-3' | SEQ No. 18 |
| | Reverse-direction primer | 5'-CCA AGT CAA GCA TGG AGG CAA TCA A-3' | SEQ No. 19 |
| dhaB2 | Forward-direction primer | 5'-GGA GCT AAT CGC TGG TGT TGA AGA-3' | SEQ No. 20 |
| | Reverse-direction primer | 5'-CCA AGT CGA TAT GTA AGG TGA CAG GT-3' | SEQ No. 21 |
| dhaB3 | Forward-direction primer | 5'-CTA TGA GAG TTC AGG ATT ACC CAC T-3' | SEQ No. 22 |
| | Reverse-direction primer | 5'-CCC TTT CTT AGC TTA TGT CTT TGT TGG T-3' | SEQ No. 23 |
| gdrA | Forward-direction primer | 5'-GAG GGT TGG ATT GTT TTG ATC GAT GA-3' | SEQ No. 24 |
| | Reverse-direction primer | 5'-CCT CTA ATA TCT CTG ACA GGA GCA-3' | SEQ No. 25 |
| gdrB | Forward-direction primer | 5'-TCT TTC CCC TCC AGG TGT CAG GT-3' | SEQ No. 26 |
| | Reverse-direction primer | 5'-CGG ACA ATG GCA AAA CCT TCA CCA-3' | SEQ No. 27 |
| aldH | Forward-direction primer | 5'-CTG ACT TGA TGG AAG CCC ACG CT-3' | SEQ No. 28 |
| | Reverse-direction primer | 5'-GGA ACC TGT GAA GGC AAT AGC GTC A-3' | SEQ No. 29 |
| KGSadh | Forward-direction primer | 5'-CGA TGC CAT TGC TCA ACT TAT GAC TCA-3' | SEQ No. 30 |
| | Reverse-direction primer | 5'-CCA AAC CAA TCA CGC CAG CTG GA-3' | SEQ No. 31 |

TABLE 3

| | Exp. 1* | Exp. 2* |
|---|---|---|
| Host | KM36907 | KM36907 |
| Expression vector | pJSKM-316 | pJSKM-316 |
| Promoter | GPD promoter | GPD promoter |
| Terminator | CYC1 terminator | CYC1 terminator |
| Number of genes | 6 types* (dhaB1, B2, B3, gdrA, gdrB, aldH) | 6 types* (dhaB1, B2, B3, gdrA, gdrB, KGSadh) |
| Gene co-integration efficiency | 28.8% | 100% |
| Strain preparation time | 6 days | 5 days |

*Exp. 1 shows 6-gene co-integration efficiency and co-integrated strain preparation time of *K. marxianus* when $OD_{600}$ is 1.
*Exp. 2 shows 6-gene co-integration efficiency and co-integrated strain preparation time of *K. marxianus* when $OD_{600}$ is 3.5.
*dhaB1 (SEQ No. 11), dhaB2 (SEQ No. 12), dhaB3 (SEQ No. 13), gdrA (SEQ No. 14), gdrB (SEQ No. 15), aldH (SEQ No. 16), KGSadh (SEQ No. 17).

When the method of the embodiments is used, genes may be more efficiently co-integrated into microbial organism to prepare a recombinant yeast strain than the conventional method. When the multiple genes co-integration technology is used, the strain preparation time of the new technology was lower by 4 times (6 days according to an embodiment) than strain preparation time of the conventional technology (27 days). Accordingly, by using the efficient multiple genes co-integration technology, various types of genes may be co-integrated into the microbial organism more effectively.

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and "at least one" and similar referents in the context of describing the invention (especially in the context of the following claims) are to be construed to cover both the singular and the plural, unless otherwise indicated herein or clearly contradicted by context. The use of the term "at least one" followed by a list of one or more items (for example, "at least one of A and B") is to be construed to mean one item selected from the listed items (A or B) or any combination of two or more of the listed items (A and B), unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

What is claimed is:

1. A method of simultaneous co-integration of multiple nucleic acid sequences into a genome of a microbial organism comprising:

culturing a microbial organism to be transformed until a growth phase is reached in which a random integration is facilitated, wherein during the growth phase in which random integration is facilitated, the microbial organism has a cell density greater than its cell density during its log phase of growth, and wherein the growth phase is a stationary phase; and transforming the microbial organism by mixing the cultured microbial organism with a sample to be co-integrated into the microbial organism with, wherein the sample comprises multiple nucleic acid fragments encoding different gene products, wherein the microbial organism to be transformed is a strain having a dominant non-homologous end joining (NHEJ) system, wherein the multiple nucleic acid fragments are linear nucleic acid fragments comprising a promoter, an open reading frame encoding a gene product, and a terminator, and the gene product is at least part of an enzyme participating in a metabolic pathway of the microbial organism, and the metabolic pathway is related to a synthesis of one or more organic acids.

2. The method of claim 1, wherein during the growth phase in which the random integration is initiated, the microbial organism has an optical density at 600 nm (OD600) of about 2.0 to about 10.0.

3. The method of claim 2, wherein the OD600 is about 3.5 to about 6.0.

4. The method of claim 1, wherein the microbial organism to be transformed is a non-conventional yeast, or fungi cell.

5. The method of claim 1, wherein the microbial organism to be transformed is *K. marxianus*.

6. The method of claim 1, wherein the sample comprises 2 to 10 of the multiple nucleic acid fragments encoding different gene products.

7. The method of claim 6, wherein the sample comprises 3 to 6 of the multiple nucleic acid fragments encoding different gene products.

8. The method of claim 1 further comprising co-integrating multiple copies of a nucleic acid sequence into the microbial organism.

* * * * *

SEQUENCE LISTING

```
<160> NUMBER OF SEQ ID NOS: 31

<210> SEQ ID NO 1
<211> LENGTH: 6544
<212> TYPE: DNA
<213> ORGANISM: Artificial Sequence
<220> FEATURE:
<223> OTHER INFORMATION: Synthetic (pJSKM316-GPD sequence)

<400> SEQUENCE: 1
tcgcgcgttt cggtgatgac ggtgaaaacc tctgacacat gcagctcccg gagacggtca    60
cagcttgtct gtaagcggat gccgggagca gacaagcccg tcagggcgcg tcagcgggtg   120
ttggcgggtg tcggggctgg cttaactatg cggcatcaga gcagattgta ctgagagtgc   180
accacgcttt tcaattcaat tcatcatttt ttttttattc tttttttttga tttcggtttc   240 tttgaaattt ttttgattcg gtaatctccg aacagaagga agaacgaagg aaggagcaca   300
gacttagatt ggtatatata cgcatatgta gtgttgaaga acatgaaat tgcccagtat    360 tcttaaccca actgcacaga acaaaaacct gcaggaaacg aagataaatc atgtcgaaag   420
ctacatataa ggaacgtgct gctactcatc ctagtcctgt tgctgccaag ctatttaata   480
tcatgcacga aaagcaaaca aacttgtgtg cttcattgga tgttcgtacc accaaggaat   540
tactggagtt agttgaagca ttaggtccca aaatttgttt actaaaaaca catgtggata   600
tcttgactga ttttccatg gagggcacag ttaagccgct aaaggcatta tccgccaagt    660
acaatttttt actcttcgaa gacagaaaat ttgctgacat tggtaataca gtcaaattgc   720
agtactctgc gggtgtatac agaatagcag aatgggcaga cattacgaat gcacacggtg   780
tggtgggccc aggtattgtt agcggtttga agcaggcggc agaagaagta acaaaggaac   840
ctagaggcct tttgatgtta gcagaattgt catgcaaggg ctccctatct actggagaat   900
atactaaggg tactgttgac attgcgaaga gcgacaaaga ttttgttatc ggctttattg   960
ctcaaagaga catgggtgga agagatgaag gttacgattg gttgattatg acacccggtg  1020
tgggtttaga tgacaaggga gacgcattgg gtcaacagta tagaaccgtg gatgatgtgg  1080
tctctacagg atctgacatt attattgttg gaagaggact atttgcaaag ggaagggatg  1140
ctaaggtaga gggtgaacgt tacagaaaag caggctggga agcatatttg agaagatgcg  1200
gccagcaaaa ctaaaaaact gtattataag taaatgcatg tatactaaac tcacaaatta  1260
gagcttcaat ttaattatat cagttattac cctgcggtgt gaaataccgc acagatgcgt  1320
aaggagaaaa taccgcatca ggaaattgta aacgttaata ttttgttaaa attcgcgtta  1380
aatttttgtt aaatcagctc attttttaac caataggccg aaatcggcaa aatcccttat  1440
aaatcaaaag aatagaccga gatagggttg agtgttgttc cagtttggaa caagagtcca  1500
ctattaaaga acgtggactc caacgtcaaa gggcgaaaaa ccgtctatca gggcgatggc  1560
ccactacgtg aaccatcacc ctaatcaagt tttttggggt cgaggtgccg taaagcacta  1620
```

```
aatcggaacc ctaaagggag cccccgattt agagcttgac ggggaaagcc ggcgaacgtg     1680
gcgagaaagg aagggaagaa agcgaaagga gcgggcgcta gggcgctggc aagtgtagcg     1740
gtcacgctgc gcgtaaccac cacacccgcc gcgcttaatg cgccgctaca gggcgcgtcg     1800
cgccattcgc cattcaggct gcgcaactgt tgggaagggc gatcggtgcg ggcctcttcg     1860
ctattacgcc agctggcgaa ggggggatgt gctgcaaggc gattaagttg ggtaacgcca     1920
gggttttccc agtcacgacg ttgtaaaacg acggccagtg aattgtaata cgactcacta     1980
tagggcgaat tggagctcca ccgcggtggc ggccgcagtt tatcattatc aatactcgcc     2040
atttcaaaga atacgtaaat aattaatagt agtgattttc ctaactttat ttagtcaaaa     2100
aattagcctt ttaattctgc tgtaacccgt acatgcccaa ataggggggc gggttacaca     2160
gaatatataa catcgtaggt gtctgggtga acagtttatt cctggcatcc actaaatata     2220
atggagcccg cttttttaagc tggcatccag aaaaaaaaag aatcccagca ccaaaatatt     2280
gttttcttca ccaaccatca gttcataggt ccattctctt agcgcaacta cagagaacag     2340
gggcacaaac aggcaaaaaa cgggcacaac ctcaatggag tgatgcaacc tgcctggagt     2400
aaatgatgac acaaggcaat tgacccacgc atgtatctat ctcattttct tacaccttct     2460 attccttct gctctctctg atttggaaaa agctgaaaaa aaaggttgaa accagttccc     2520
tgaaattatt cccctacttg actaataagt atataaagac ggtaggtatt gattgtaatt     2580
ctgtaaatct atttcttaaa cttcttaaat tctactttta tagttagtct ttttttttagt     2640 tttaaaacac cagaacttag tttcgacgga ttctagaact agtggatccc ccgggctgca     2700
ggaattcgat atcaagctta tcgataccgt cgacctcgag tcatgtaatt agttatgtca     2760
cgcttacatt cacgccctcc ccccacatcc gctctaaccg aaaaggaagg agttagacaa     2820
cctgaagtct aggtccctat ttattttttt atagttatgt tagtattaag aacgttattt     2880
atatttcaaa ttttctttt ttttctgtac agacgcgtgt acgcatgtaa cattatactg     2940
aaaaccttgc ttgagaaggt tttgggacgc tcgaaggctt taatttgcgg ccggtaccca     3000
gcttttgttc cctttagtga gggttaattc cgagcttggc gtaatcatgg tcatagctgt     3060
ttcctgtgtg aaattgttat ccgctcacaa ttccacacaa cataggagcc ggaagcataa     3120
agtgtaaagc ctggggtgcc taatgagtga ggtaactcac attaattgcg ttgcgctcac     3180
tgcccgcttt ccagtcggga aacctgtcgt gccagctgca ttaatgaatc ggccaacgcg     3240
cggggagagg cggtttgcgt attgggcgct cttccgcttc ctcgctcact gactcgctgc     3300
gctcggtcgt tcggctgcgg cgagcggtat cagctcactc aaaggcggta atacggttat     3360
ccacagaatc aggggataac gcaggaaaga acatgtgagc aaaaggccag caaaaggcca     3420
ggaaccgtaa aaaggccgcg ttgctggcgt ttttccatag gctcggcccc cctgacgagc     3480
atcacaaaaa tcgacgctca agtcagaggt ggcgaaaccc gacaggacta taaagatacc     3540
aggcgttccc ccctggaagc tccctcgtgc gctctcctgt tccgaccctg ccgcttaccg     3600
gatacctgtc cgcctttctc ccttcgggaa gcgtggcgct ttctcaatgc tcacgctgta     3660
ggtatctcag ttcggtgtag gtcgttcgct ccaagctggg ctgtgtgcac gaaccccccg     3720
ttcagcccga ccgctgcgcc ttatccggta actatcgtct tgagtccaac ccggtaagac     3780
acgacttatc gccactggca gcagccactg gtaacaggat tagcagagcg aggtatgtag     3840
gcggtgctac agagttcttg aagtggtggc ctaactacgg ctacactaga aggacagtat     3900
ttggtatctg cgctctgctg aagccagtta ccttcggaaa aagagttggt agctcttgat     3960
ccggcaaaca aaccaccgct ggtagcggtg gtttttttgt ttgcaagcag cagattacgc     4020
```

```
gcagaaaaaa aggatctcaa gaagatcctt tgatcttttc tacggggtct gacgctcagt   4080
ggaacgaaaa ctcacgttaa gggattttgg tcatgagatt atcaaaaagg atcttcacct   4140
agatcctttt aaattaaaaa tgaagtttta aatcaatcta agtatatat gagtaaactt    4200 ggtctgacag ttaccaatgc ttaatcagtg aggcacctat ctcagcgatc tgtctatttc   4260
gttcatccat agttgcctga ctgcccgtcg tgtagataac tacgatacgg gagggcttac   4320
catctggccc cagtgctgca atgataccgc gagacccacg ctcaccggct ccagatttat   4380
cagcaataaa ccagccagcc ggaagggccg agcgcagaag tggtcctgca actttatccg   4440
cctccatcca gtctattaat tgttgccggg aagctagagt aagtagttcg ccagttaata   4500
gtttgcgcaa cgttgttgcc attgctacag gcatcgtggt gtcacgctcg tcgtttggta   4560
tggcttcatt cagctccggt tcccaacgat caaggcgagt tacatgatcc cccatgttgt   4620 gaaaaaagc ggttagctcc ttcggtcctc cgatcgttgt cagaagtaag ttggccgcag    4680
tgttatcact catggttatg gcagcactgc ataattctct tactgtcatg ccatccgtaa   4740
gatgcttttc tgtgactggt gagtactcaa ccaagtcatt ctgagaatag tgtatgcggc   4800
gaccgagttg ctcttgcccg gcgtcaatac gggataatac cgcgccacat agcagaactt   4860
taaaagtgct catcattgga aaacgttctt cggggcgaaa actctcaagg atcttaccgc   4920
tgttgagatc cagttcgatg taacccactc gtgcacccaa ctgatcttca gcatctttta   4980
cttttaccag cgtttctggg tgagcaaaaa caggaaggca aaatgccgca aaaagggaa    5040 taagggcgac acggaaatgt tgaatactca tactcttcct ttttcaatat tattgaagca   5100
tttatcaggg ttattgtctc atgagcggat acatatttga atgtatttag aaaaataaac   5160
aaataggggt tccgcgcaca tttccccgaa aagtgccacc tgacgtcgag ctcctttcat   5220
ttctgataaa agtaagatta ctccatttat cttttcacca acatattcat agttgaaagt   5280
tatccttcta agtacgtata caatattaat taaacgtaaa aacaaactg actgtaaaaa    5340 tgtgtaaaaa aaaatatca aattcatagc agtttcaagg aatgaaaact attatgatct    5400
ggtcacgtgt atataaatta ttaattttaa acccatataa tttattattt ttttattcta   5460
aagtttaaag taatttagt agtatttat attttgaata aatatacttt aaattttat      5520 ttttatattt tattacttt aaaaataatg tttttattta aaacaaaatt ataagttaaa    5580
aagttgttcc gaaagtaaaa tatatttat agttttttaca aaaataaatt attttaacg    5640 tattttttt aattatattt ttgtatgtga ttatatccac aggtattatg ctgaatttag    5700
ctgtttcagt ttaccagtgt gatagtatga ttttttttgc ctctcaaaag ctattttttt   5760
agaagcttcg tcttagaaat aggtggtgta taaattgcgg ttgacttta actatatatc    5820 attttcgatt tatttattac atagagaggt gcttttaatt ttttaatttt tattttcaat   5880 aatttaaaa gtgggtactt ttaaattgga acaaagtgaa aaatatctgt tatacgtgca    5940
actgaatttt actgacctta aaggactatc tcaatcctgg ttcagaaatc cttgaaatga   6000
ttgatatgtt ggtggatttt ctctgatttt caaacaagag gtatttatt tcatatttat    6060 tatattttt acatttattt tatattttt tattgtttgg aagggaaagc gacaatcaaa     6120
ttcaaaatat attaattaaa ctgtaatact taataagaga caaataacag ccaagaatca   6180
aatactgggt ttttaatcaa agatctctc tacatgcacc caaattcatt atttaaattt    6240
actatactac agacagaata tacgaaccca gattaagtag tcagacgctt ttccgcttta   6300
ttgagtatat agccttacat attttctgcc cataatttct ggatttaaaa taaacaaaaa   6360
```

```
tggttacttt gtagttatga aaaaaggctt ttccaaaatg cgaaatacgt gttatttaag    6420
gttaatcaac aaaacgcata tccatatggg tagttggaca aaacttcaat cgatgacgtc    6480
taagaaacca ttattatcat gacattaacc tataaaaata ggcgtatcac gaggcccttt    6540
cgtc                                                                 6544

<210> SEQ ID NO 2
<211> LENGTH: 1503
<212> TYPE: DNA
<213> ORGANISM: Artificial Sequence
<220> FEATURE:
<223> OTHER INFORMATION: Synthetic (ALD6 sequence)

<400> SEQUENCE: 2
atgactaagc tacactttga cactgctgaa ccagtcaaga tcacacttcc aaatggtttg      60 acatcgagc aaccaaccgg tctattcatt aacaacaagt ttatgaaagc tcaagacggt     120
aagacctatc ccgtcgaaga tccttccact gaaaacaccg tttgtgaggt ctcttctgcc     180
accactgaag atgttaatta tgctatcgaa tgtgccgacc gtgctttcca cgacactgaa     240
tgggctaccc aagacccaag agaaagaggc cgtctactaa gtaagttggc tgacgaattg     300
gaaagccaaa ttgacttggt ttcttccatt gaagctttgg acaatggtaa aactttggcc     360
ttagcccgtg gggatgttac cattgcaatc aactgtctaa gagatgctgc tgcctatgcc     420
gacaaagtca cggtagaac aatcaacacc ggtgacggct acatgaactt caccacctta     480
gagccaatcg gtgtctgtgg tcaaattatt ccatggaact ttccaataat gatgttggct     540
tggaagatcg cccagcatt ggccatgggt aacgtctgta tcttgaaacc cgctgctgtc     600 acactttaa atgccctata ctttgcttct ttatgtaaga aggttggtat tccagctggt     660
gtcgtcaaca tcgttccagg tcctggtaga actgttggtg ctgctttgac caacgaccca     720
agaatcagaa agctggcttt taccggttct acagaagtcg gtaagagtgt tgctgtcgac     780
tcttctgaat ctaacttgaa gaaaatcact ttggaactag gtggtaagtc cgcccatttg     840
gtctttgacg atgctaacat taagaagact ttaccaaatc tagtaaacgg tattttcaag     900
aacgctggtc aaatttgttc ctctggttct agaatttacg ttcaagaagg tatttacgac     960
gaactattgg ctgctttcaa ggcttacttg gaaaccgaaa tcaaagttgg taatccattt    1020
gacaaggcta acttccaagg tgctatcact aaccgtcaac aattcgacac aattatgaac    1080
tacatcgata tcggtaagaa agaaggcgcc aagatcttaa ctggtggcga aaaagttggt    1140
gacaagggtt acttcatcag accaaccgtt ttctacgatg ttaatgaaga catgagaatt    1200
gttaaggaag aaattttggg accagttgtc actgtcgcaa agttcaagac tttagaagaa    1260
ggtgtcgaaa tggctaacag ctctgaattc ggtctaggtt ctggtatcga aacagaatct    1320
ttgagcacag gtttgaaggt ggccaagatg ttgaaggccg gtaccgtctg gatcaacaca    1380
tacaacgatt ttgactccag agttccattc ggtggtgtta agcaatctgg ttacggtaga    1440
gaaatgggta agaagtcta ccatgcatac actgaagtaa aagctgtcag aattaagttg    1500
taa                                                                 1503

<210> SEQ ID NO 3
<211> LENGTH: 2055
<212> TYPE: DNA
<213> ORGANISM: Artificial Sequence
<220> FEATURE:
<223> OTHER INFORMATION: Synthetic (ACS2 sequence)

<400> SEQUENCE: 3
```

```
atggtattag gaaaggctca caagattgtg cacgaagcac acgaagttt ggcccgccat    60 gcgccagaac atttctacaa gtcgcaacca ggcaagtcgt actgtgcgga tgaagaacag   120
taccgccaaa tgtacagcca atcgatcaac gacccaagcg gcttttttgg acccttggct   180
aaggagtact tgcactggga ccgcccattc acgcaagtgc aaagcggttc gttggaacac   240
ggcgatgttg cgtggttttt gaacggtgag ttgaacgcct cgtataactg tgttgataga   300
cacgcgtttg ccaacccaga caagccagct ttgatctacg aagccgacga cgaatctgaa   360
aacaaggtca tcacctttgg cgaattgttg agacaggtct ctgaagtcgc tggtgtcttg   420
aagtcatggg gtgtcaagaa gggtgacacc gttgctgtgt atttgccaat gattccagcc   480
gctgttgttg ccatgttggc tgttgccaga ttgggtgcca tccactctgt catctttgct   540
ggtttctcag ccggttcctt gaaggaaaga gtcgtcgatg ctggctgtaa agttgtcatc   600
acctgcgatg agggtaagag aggtggtaaa acggtccaca ccaagaagat tgttgacgaa   660
ggtttggctg gtgtcgactc cgttgccaag atcttggtct ccaaagaac tggtaccgtt   720 ggcatcccaa tgaagccagg tagagatttc tggtggcacg aggaatgtgt caagcaaaag   780
ggttacctac cacctgtccc agttaactct gaggacccat tgttcttgct atacacttcc   840
ggttccaccg ttctccaaa gggtgttgtt cactccaccg caggttactt gttgggttcc   900
gcattgacca ccagatatgt cttcgatatc cacccagaag atgtcttgtt taccgctggt   960
gacgtcggtt ggattaccgg tcacacttat gctttgtatg gtccattgac tcttggtacc  1020
gccaccatca tctttgaatc caccctgcc tacccagatt acggtagata ctggagaatc  1080
atcgaacgtc acagagctac ccacttctac gttgccccaa ccgcgctaag attgatcaag  1140
cgtgttggtg aacaggaaat cgccaagtac gacacctctt ccttgagagt gttgggttct  1200
gttggtgagc caatctcccc agatctatgg gaatggtatc acgaaaaggt cggtaacaag  1260
aattgtgtca tctgtgacac catgtggcaa accgaatctg gttcccactt gatcgctcca  1320
ttggcaggtg ctgtgccaac caagccaggt tccgctaccg ttccattctt tggtatcaac  1380
gcatgcatca tcgacccagt ctccggtgaa gagttgacag gtaacgatgt cgaaggtgtc  1440
ttggccgtca agtccccatg gccttcaatg gccagatctg tctggaacaa tcactcccgt  1500
tacttcgaaa cctacttgaa gccataccct ggttactact tcaccggtga cggtgctggt  1560
agagaccacg acggttacta ctggatcaga ggtagagttg acgatgtcgt gaacgtctcc  1620
ggtcacagac tatctaccgc tgaaatcgaa gccgccttgg tcgaacacga aggtgtctca  1680
gaatctgccg tcgttggtat caccgacgaa cttacaggtc aagctgttat cgcctttgtc  1740
tccttgaagg acggttacct agccgaagac gcagtagaag gtgacccagc ccacatctcc  1800
ccagacaagc tacgtcgtga gctaatctta caagttagag gtgaaattgg tccattcgct  1860
gcaccaaaga ccgttgtcat tgtcaacgac ttgccaaaga caagatcagg taagatcatg  1920
agaagagtct tgagaaagat cgcttcaaag gaagccgacc aattgggtga cctaagtaca  1980
cttgctaacc cagatgttgt tccatctatt atctcaagtg tcgaaaccca attctttaac  2040
caacaaaaga aataa                                                    2055
```

<210> SEQ ID NO 4
<211> LENGTH: 6699
<212> TYPE: DNA
<213> ORGANISM: Artificial Sequence
<220> FEATURE:
<223> OTHER INFORMATION: Synthetic (ACC sequence)

```
<400> SEQUENCE: 4
atgagtgaag aaaatctttc tgaggtttcc atttctcaga gccaacagta tgaagttact      60
gacttcagtc acagacattc aaaactagcg ccacatttca tcgggttaaa cactgttgac     120
aaagtcgaag attctccatt aaaggaattt gttaaatcac atggcggtca tacagtcatc     180
tcaaaaatct tgatcgcaaa caatggtatt gctgccgtaa aagagatcag atccgtacgt     240
aagtggtctt acgaaatttt tggcgatgaa ggactgtac aattcgtagc aatggctaca      300
ccagaagatc ttgaagcaaa tgcggaatac atccgtatgg ctgatcagta tatcgaagtt     360
ccaggtggaa caaataacaa taactacgct aacgtcgacc ttatcgtaga agttgctgaa     420
agagccgatg ttgatgccgt ttgggctggt tggggtcatg cttccgaaaa tcctctgctt     480
ccagaaagat tggctgcttc caagagaaaa atcatcttta ttggtccacc aggtaacgca     540
atgagatctc taggtgacaa gatttcgtca actattgtcg cccaacatgc caaggttcca     600
tgtattccat ggtcaggtac tggcgtcgat gaagtccaca tagataagga aactaaccta     660
gtttctgtcg atgaagaagt ataccaaaaa ggttgctgtt cctctccaga agatggttta     720
aagaaagcta acaaattgg ctttccagtg atgatcaagg catcagaagg tggtggtggt      780
aaaggtatca gaaggtcga aaatgaagaa gaattccttt cattgtatca acaagctgct      840
aacgaaattc caggttctcc aatttttcatt atgaagttgg ctggtaaagc ccgtcatttg     900
gaagttcaat tgcttgctga tcaatacggt actaatattt ctctattcgg tcgtgactgt     960
tccgttcaaa gacgtcatca aaaaatcatc gaagaagccc ctgtcactat tgcaaagcct    1020
caaacattca cagaaatgga aaaggcagct gttagattag gtcaattagt cggttacgtg    1080
tctgcaggta cagttgaata cttatactcg catgacgagg ataagttcta cttcttggaa    1140
ttaaacccaa gattacaagt ggagcatcca actaccgaaa tggtcacagg tgtgaactta    1200
ccagcagctc agttgcaaat tgcaatgggt atcccaatgc atagaattag agacattaga    1260
ttgctttacg gtgtcgatcc aaagagcgcc tcggagattg atttcgaatt ttccactcca    1320
gaatcttcca agactcaaag aaaaccaatc cctaagggtc actgtactgc ttgtcgtatc    1380
acttctgaag atccaaatga aggtttcaag ccatcaggtg gtgctttaca cgaactaaac    1440
ttccgttctt cttctaacgt ttggggttat ttctctgttg gtaataacgg tggtatccac    1500
tcgttctcag attctcaatt tggtcatatt ttcgccttcg gagagaatag acaggcttcc    1560
agaaagcata tggttgttgc attgaaggag ttatcgatta gaggtgattt cagaactact    1620
gttgaatatt tgatcaaatt gttggagact gaagacttcg aagacaacac catcactact    1680
ggttggttag atgatttgat ctcccaaaag atgacagctg aaaagcctga tccaactcta    1740
tcagtcatct gtggtgcagc aaccaaggct cacattgcct cagaacaagc cagacaagaa    1800
tatattgctt ccttgaaaag aggtcaagtt cctaacaaat cctgttaca aaccatgtat     1860
cctatagagt tcattcacga tggaatgaga tacaaattca ctgttgctaa atctgcagat    1920
gaccgttaca ccctatttat taatggttcg aagtgtgaag ttggtgcaag aaaactttcc    1980
gacggtggtt tactaattgc agttggtggt aaatcccata ctatctactg gaggaagag    2040
gtttctgcta caagactatc cattgattcc aagactaccc tattagaggt cgaaaatgat    2100
cctactcaat taagaacccc atcgccaggt aagttggtga agttttagt tgaaaatggc    2160
gaccatgtca ttgcaggaca accttatgct gaagttgaag ttatgaaaat gcaaatgcca    2220
ttgatttctc aagaaaatgg tattgttcaa cttttgaaac agcctggttc gactcttgca    2280
gctggtgata ttcttgccat tttatctttg gatgatccaa gtaaggtaaa acacgcaaag    2340
```

-continued

```
ccatacgaag gtatgttacc tgaaatgggc tcaccaattg ttgaaggtac caagccagct      2400
tacaagttca atctttagt cactaccttg gaaatatttt tgaagggata tgataaccaa      2460
gttattatga aaacttcctt gcaacagttg attgaagtat tgagacaacc agagcttcct      2520
tattctgaat ggaaattgca ggtttctgcc ttgcattcca gacttcctcc tcatttagat      2580
gaacaacaag aacaactagt tagccgctct ttcaagagag gtgctgattt cccagcaaga      2640
caattgggta gatgtttga agctgctcta aatgaccta atgtcgatcc acttttccac       2700
accaccatcg aaccacttct tgacatcact aatcgttatt ctaacggttt ggcttctcat      2760
gaacatttcg tgtttgcgac gttcttagag aattattaca atgtcgaaaa gttgttctcg      2820
ggctccaatg ttcgtgaaga agatgtcatc ttaagactac gtgatgagaa cccagatgat      2880
ttggacaagg ttgttctgac tgttcttgcc cattctagag tttctgccag aaacaacttg      2940
atattggcaa ttttgaagca ttaccaacct ttgtgcaaat tgaagtctga aattgctgcc      3000
gccattgaga aaccattaaa gcatattgtc gaattggaat caaaggctac tgcaaaggtt      3060
gctctacaag ccagagaaat tttaattcaa ggtgctctac catccattaa ggagagaacg      3120
gaccaaattc aatacatatt aaagtcttct gttttgagca cttcatatgg ttcgactgaa      3180
agcaaacgca ctaaacctga tttagaagtt ttgaaggact tgattgactc aaactacgtc      3240
gtgtttgatg ttttatctca attttttgact aactctgacg acgctgttgc agccgcagcc    3300
gctgaagtct acatcagaag agcatacaga gcttacacaa ttggggactt gaagcatttc      3360
aagacctctg gctctccagt ggtcgaatgg aagttccaac taccatctgc agcatttact      3420
tctatgcctc aagtcaagag taagttgggt atgaacagag caatctccgt ttccgatttg      3480
acatacgttt ccgaaggcga gaaccaacca ctgagaactg gtttgttgat tcctgccaaa      3540
catcttgatg atgttgacgg aatcctatca tctgctctct ctatgattcc tcctcaccat      3600
gtgtctactg gaccagctcc agatagatca ggctcttctt ctgctagctt gtctaatgtt      3660
gccaatgttg tggttaattc tactgaagga tttgaatctg agtctgaagt gttactaaga      3720
ttaaaggaga tcttagactt gaacaaacag gctcttgtag aatctgctat ccgtcgtatc      3780
acatttgtgt ttggttacag cgatggtact tatccaaaat actatacttt ccgtggtcca      3840
aactacaatg aagatgagac tattcgtcat atagaacctg cattggcttt ccaacttgag      3900
ttgggtaaaa tgtcgaactt taacattaga caaatcttta ccgagaacag aaacatccac      3960
gtatatgaag ctgttggtaa gaactctcct gtagacaaga gattcttcac aagaggtatc      4020
attgaaaccg tcgtattcg cgatgacatc tcaattgttg aatatttgac ttctgaagca      4080
aatagattga tgagtgacat cttggataac ttagaaatta tcgacaccctc caattccgac     4140 ttgaatcata tcttcatcaa cttttctgct gttttcgatg tttctccaga agatgtggaa      4200
gctgcattcg gtggcttctt ggaaagattt ggtagaagat tattgagact tcgtgttgct      4260
gctgctgaga ttagaatcat catcaaagac cctcaaacag gtacaccagt tcccctaaga      4320
gctttgatta acaatgtttc tggatttgtt gtcaaaactg aattgtacac ggaagtgaag      4380
aatgcccaag gtgagtggat ctttaagtct ttagacaagc ctggttccat gcacttaaga      4440
ccaattgcaa caccataccc cgctaaggag tggttgcaac ctaagcgtta caaggcccat      4500
ctaatgggta ctacttatgt ttacgatttc cccgaattgt tccgccaagc tattgttact      4560
caatggaaga agtattctcc aaagaagaaa ttgtctgatg acttctttat tgctaacgaa      4620
ttgattgaag acgaaaatgg agaactcact gaagttgatc gtgaattagg tgcaaacaac      4680
```

```
attggtatgg ttgctttcaa ggtgacagct aagactccag aatacccaca tggtcgtcaa   4740
ttcgtgattg ttgcaaacga tatcacctac aaaatcggtt ctttcggtcc acaagaagat   4800
gaattcttca acaaggttac tgagtatgca agaaagagag gtattccacg tgtctacttg   4860
tctgccaact ctggtgctag aattggcatt gctgaagagt tggttccatt attccaaatt   4920
gcatggaatg atgaaaaaga tccttctaag ggtttccaat acttatggct cacagatgaa   4980
gctttggaag aactcagagc ccaaggtaag gaaaactctg ttgttactca acgtgttgtc   5040
gaagaaggaa aggcaagaaa tattatcact gctattattg gtagcgaaga tggtcttggt   5100
gttgagtgtt tgaagggttc aggtttaatt gccggtgcaa cttctagggc ttacaaggac   5160
atcttcacta ttactttagt gacttgtaga tcggttggta ttggtgcata cttggttaga   5220
ctaggtcaaa gagcaattca aattgaagct caacctatca tcttgaccgg tgctcctgct   5280
attaacaagc ttttgggtag agaagtttac tcatctaact gcaattggg tggtactcaa   5340
atcatgtaca acaatggtgt ttctcactta actgcccctg atgatctagc tggtgttgag   5400
aagatcatga attggttatc ttatattcct gctaagagag atcttcctgt tcctatttta   5460
gaatctgacg ataaatggga tagacttgtc gactttacac caacaaccaa cgagcaatat   5520
gatgttagat ggatgattga aggtcgtgag actgaggaag gtttccaata tggtttgttc   5580
gataaaggct ccttccaaga aactttgtct ggctgggcta gaggtgttgt tactggtaga   5640
gctcgtttag gtggtattcc attaggtgtt attgctgtcg aaacacgtat cgttgaaaat   5700
ctaattccag ctgatccagc taacccagat tccaccgaaa tgttgattca agaggctggt   5760
caagtgtggt atccaaactc cgcttttcaag acagcccaag ctatcaacga tttcaaccac   5820
ggtgagcaat tgcctctaat gattctagca aactggagag gtttctctgg tggtcaacgt   5880
gatatgtaca atgaagtctt gaaatacggt tcttttcattg tcgatgctct agtagattat   5940
aaacaaccaa tcattactta cattccacca actggtgaat taagaggtgg ttcttgggtt   6000
gttgttgatc caactattaa tgctgaccaa atggaaatgt atgctgatat caattctaga   6060
gctggtgttc tagaacctga aggtatggtt ggtatcaaat accgtagaga aaagttgcta   6120
gctactatgg ctaggttgga cgacaagtat agagctttga aggacagatt cgcaaaccct   6180
gacttaaccc cagaggaaca ccaacaagtc tctaaggagc ttgctgaacg tgagaagcaa   6240
ctactaccaa tctatcacca aatcactgtt caattcgctg atttacatga taggtctggt   6300
cgtatgttgg caaagggtgt aatcagaaaa gagctgaact ggccagaatc ccgtcgtttc   6360
ttcttctgga gattaagaag aagattaaat gaagagtacc taatgagaag attgaacaat   6420
gagctaggat cagcctcaag attggagaag atggctagaa ttagatcatg gtaccctgca   6480
tccgtcagct tggatgacga tagacaagtt gctacttgga tcgaagagaa ctatcaactc   6540
ctagatgaac aaatcaagag tgttaagcta gaagcctttg cacaaaactt ggctaaatct   6600
atcagaaatg accatgataa ctctattaac ggttttggctg aagtcttgaa gctcttatct   6660
gttaaggaca aagaaaagct tcaaaaggct ttggaatga                           6699
```

<210> SEQ ID NO 5
<211> LENGTH: 26
<212> TYPE: DNA
<213> ORGANISM: Artificial Sequence
<220> FEATURE:
<223> OTHER INFORMATION: Synthetic (forward primer for ALD6)

<400> SEQUENCE: 5
cattatcaat actcgccatt tcaaag    26

<210> SEQ ID NO 6
<211> LENGTH: 27
<212> TYPE: DNA
<213> ORGANISM: Artificial Sequence
<220> FEATURE:
<223> OTHER INFORMATION: Synthetic (reverse primer for ALD6)

<400> SEQUENCE: 6
ttacaactta attctgacag cttttac                                27

<210> SEQ ID NO 7
<211> LENGTH: 26
<212> TYPE: DNA
<213> ORGANISM: Artificial Sequence
<220> FEATURE:
<223> OTHER INFORMATION: Synthetic (forward primer for ACS2)

<400> SEQUENCE: 7
cattatcaat actcgccatt tcaaag                                 26

<210> SEQ ID NO 8
<211> LENGTH: 28
<212> TYPE: DNA
<213> ORGANISM: Artificial Sequence
<220> FEATURE:
<223> OTHER INFORMATION: Synthetic (reverse primer for ACS2)

<400> SEQUENCE: 8
ttatttcttt tgttggttaa gaattggg                               28

<210> SEQ ID NO 9
<211> LENGTH: 26
<212> TYPE: DNA
<213> ORGANISM: Artificial Sequence
<220> FEATURE:
<223> OTHER INFORMATION: Synthetic (forward primer for ACC)

<400> SEQUENCE: 9
cattatcaat actcgccatt tcaaag                                 26

<210> SEQ ID NO 10
<211> LENGTH: 31
<212> TYPE: DNA
<213> ORGANISM: Artificial Sequence
<220> FEATURE:
<223> OTHER INFORMATION: Synthetic (reverse primer for ACC)

<400> SEQUENCE: 10
tcattccaaa gcctttttgaa gcttttcttt g                          31

<210> SEQ ID NO 11
<211> LENGTH: 1668
<212> TYPE: DNA
<213> ORGANISM: Artificial Sequence
<220> FEATURE:
<223> OTHER INFORMATION: Synthetic (dhaB1 sequence)

<400> SEQUENCE: 11
atgaaaagat ctaagaggtt cgctgttcta gctcaaggc ctgttaatca ggacggacta     60
attggtgaat ggccagaaga aggtcttatc gccatggaca gtccattcga cccagttttct   120 tcagttaagg ttgacaacgg cttgattgtg gagttggatg gtaagcgtag agatcagttc   180
gacatgatag atagattcat tgcagactac gctattaatg tggaaagaac cgagcaggcc   240

```
atgagattag aagctgttga gatcgcaaga atgctagtcg acattcacgt gtcaagagaa      300
gagatcatcg caattaccac tgctattact ccagctaagg ctgttgaagt gatggcacaa      360
atgaacgtcg ttgaaatgat gatggctttg cagaaaatga gagcacgtag aacaccttct      420
aaccaatgcc atgtcaccaa cttgaaagat aatccagtgc aaattgctgc tgatgctgcc      480
gaagctggta ttcgtggctt ctccgaacaa gaaaccaccg ttggtatcgc tagatatgct      540
ccattcaacg cactagcttt gttggttggt tctcaatgtg gtagaccagg tgtcttgact      600
caatgttctg tcgaagaagc taccgaatta gaattgggta tgagaggatt gacctcttac      660
gccgaaaccg tctctgttta cggtacgaaa gccgtcttta ctgacggtga tgacacacca      720
tggtctaagg catttcttgc ttctgcctat gcttcaagag gtttgaagat gagatacacc      780
tccggtactg gttcagaagc cttgatgggt tactccgagt ccaagtccat gttatactta      840
gagagtagat gtatcttcat taccaaggga gccggtgtcc agggcttgca aaatggtgca      900
gttagttgta ttggtatgac tggtgctgtt ccttccggaa ttagagcagt tttggccgaa      960
aacttgattg cctccatgct tgacttggag gttgcctctg caaatgacca aacttttagt     1020
cactccgata taagaagaac tgccaggaca ttgatgcaga tgttgccagg caccgatttc     1080
atcttttccg gttactctgc cgtgcctaac tacgataaca tgtttgccgg ttccaacttc     1140
gacgctgagg atttcgatga ttacaatata ctacaacgtg atttaatggt ggacggcggt     1200
ctacgtcctg ttactgaagc tgaaaccatc gctatccgtc agaaggccgc tagagctatt     1260
caagctgttt ttagagaatt aggtttgcca ccaatcgctg acgaagaggt ggaggctgct     1320
acctacgcac atggttctaa cgaaatgcca cctagaaatg ttgttgaaga tctatccgca     1380
gtggaagaga tgatgaagag aaacatcact ggtttggata tcgttggtgc attgtcaaga     1440
tccggtttcg aagatatcgc ctctaacatt ttgaacatgt tgaggcaaag agtcacaggt     1500
gactatttac aaacatcagc tatccttgac cgtcaattcg aggttgtcag tgctgtcaac     1560
gacatcaacg attatcaagg cccaggtaca ggttacagaa tctctgctga aagatgggca     1620
gaaatcaaga acatcccagg agtcgtccaa ccagacacta tagaataa                  1668
```

<210> SEQ ID NO 12
<211> LENGTH: 441
<212> TYPE: DNA
<213> ORGANISM: Artificial Sequence
<220> FEATURE:
<223> OTHER INFORMATION: Synthetic (dhaB2 sequence)

<400> SEQUENCE: 12

```
atgccacatg gtgcaatctt aaaggagcta atcgctggtg ttgaagaaga aggtttgcac       60
gctagagtgg ttagaatttt aagaacctcc gatgtttctt ttatggcctg ggacgccgcc      120
aaccttcctg gtagtggtat cggcattgga atccaatcca aaggtacaac tgttattcac      180
cagagagact tgctaccttt gtcaaacttg gagttgttct ctcaagcccc attgttgact      240
cttgagacat accgtcaaat tggtaaaaac gcagctagat atgctaggaa ggaatctcca      300
tccccagtcc cagtcgtcaa tgatcaaatg gttagaccaa agttcatggc taaggctgca      360
ttgttccaca taaaggaaac caagcatgtc gtgcaggatg ctgaacctgt caccttacat      420
atcgacttgg ttcgtgaata a                                               441
```

<210> SEQ ID NO 13
<211> LENGTH: 426
<212> TYPE: DNA
<213> ORGANISM: Artificial Sequence

```
<220> FEATURE:
<223> OTHER INFORMATION: Synthetic (dhaB3 sequence)

<400> SEQUENCE: 13
atgtcagaaa aaactatgag agttcaggat tacccactag caacaagatg tccagagcac      60
atcttgaccc ctaccggcaa gccattgacc gacattactt tggaaaaggt tttatctggt     120
gaagtgggac ctcaagacgt gagaatcagt agacaaaccc ttgagtacca agctcaaatt     180
gctgaacaaa tgcagagaca cgctgttgct agaaacttca cgcgtgccgc tgaattgatc     240
gctattccag acgaacgtat attggccatt tataacgcat tgaggccatt taggtcttct     300
caggcagaat tacttgctat cgcagatgag ttggagcata catggcacgc tactgtcaat     360
gccgctttcg tcagagaatc cgccgaagtt taccaacaaa gacataagct aagaaagggt     420
tcctaa                                                                426

<210> SEQ ID NO 14
<211> LENGTH: 1824
<212> TYPE: DNA
<213> ORGANISM: Artificial Sequence
<220> FEATURE:
<223> OTHER INFORMATION: Synthetic (gdrA sequence)

<400> SEQUENCE: 14
atgccattga ttgctggtat cgacatcggt aacgcaacta ctgaagtcgc cttggcttcc      60
gattatccac aagccagagc cttcgtggct tctggtatcg tcgctactac tggtatgaaa     120
ggaaccagag acaacatcgc tggtacttttg gctgctttgg agcaagcctt ggcaaagaca     180
ccatggtcaa tgtcagatgt gtcaaggata tacttgaacg aagccgctcc agttatcggt     240
gatgtggcca tggaaactat cacagaaact attatcaccg agtcaaccat gataggtcat     300
aatccacaaa caccaggtgg tgtgggtgtg ggcgttggta ctaccatcgc cctaggaaga     360
cttgcaacct tgcctgcagc tcaatacgcc gagggttgga ttgttttgat cgatgacgcc     420
gtggactttt tggacgctgt ctggtggttg aatgaagctc ttgacagagg tataaacgtt     480
gtggctgcca ttttaaagaa ggacgatggt gtcctagtga ataacagatt gagaaagacc     540
ctaccagtcg tggatgaagt tacattgtta gaacaagtcc cagaaggcgt catggctgct     600
gtcgaagtgg ccgcacctgg acaggttgtt aggatcttga gtaacccata cggcatcgct     660
accttcttcg gattatcccc agaggaaact caagcaatag tccctatcgc tagagctttg     720
attggcaaca gaagtgcagt ggtcttaaag actccacagg gtgatgttca atctcgtgtt     780
atcccagctg gtaatttgta catttccggt gaaaagcgta ggggcgaagc tgacgttgct     840
gaaggagctg aagcaatcat gcaagctatg tctgcttgtg ctcctgtcag agatattaga     900
ggtgaacctg gtacccacgc tggtggtatg ttggagagag ttagaaaggt tatggcatcc     960
ttgactggtc acgagatgag tgcaatctac attcaggatt gctagcagt tgacacattt    1020 atccctagaa aagttcaagg tggtatggca ggcgaatgtg ctatgaaaaa cgctgtcggt    1080
atggctgcaa tggttaaagc tgacagattg cagatgcagg ttattgctag ggaattaagt    1140
gcaagattgc aaactgaagt tgttgtcggt ggtgttgaag ctaacatggc tatcgccggt    1200
gctttgacca ctcctggttg tgccgctcca ttggctatct tggatttagg tgctggatct    1260
accgatgctg ctatcgtgaa cgctgagggt caaattaccg ccgtccacct tgccggtgcc    1320
ggaaacatgg tttcattgtt gatcaagacc gagttgggtc ttgaagatct ttccctagcc    1380
gaggccatta agaagtatcc actagccaag gttgagtccc tattctctat tcgtcatgaa    1440
```

| | |
|---|---:|
| aacggagccg ttgaattctt ccgtgaagca ctatctccag cagtcttcgc taaggttgtc | 1500 |
| tacattaagg aaggtgagtt ggttccaatt gacaacgcct ctccacttga aaaaatcaga | 1560 |
| ttggtccgta gacaggctaa agaaaaggtc tttgttacca actgcttaag agcactaaga | 1620 |
| caagtttccc caggtggttc tattagagac atcgcatttg tggttttagt cggtggttct | 1680 |
| tccttggact tcgaaattcc acaacttatt accgaagcct atctcatta cggtgttgtt | 1740 |
| gcaggtcaag gcaacattag aggtacagag ggtccaagaa atgctgtcgc aacaggtttg | 1800 |
| ttgttagccg gccaagccaa ttaa | 1824 |

```
<210> SEQ ID NO 15
<211> LENGTH: 354
<212> TYPE: DNA
<213> ORGANISM: Artificial Sequence
<220> FEATURE:
<223> OTHER INFORMATION: Synthetic (gdrB sequence)

<400> SEQUENCE: 15
```

| | |
|---|---:|
| atgagtcttt cccctccagg tgtcaggttg ttctacgatc cacgtggtca ccacgccggt | 60 |
| gcaatcaacg aattgtgttg gggtttggaa gaacaaggtg ttccatgtca accattact | 120 |
| tatgatggag gtggcgacgc tgcagctctt ggtgctttgg ctgctagatc ttccaccattg | 180 |
| agagtcggta taggtttatc tgcctccgga gaaatcgccc taacccatgc tcaattgcct | 240 |
| gccgacgctc cattagcaac cggtcatgtt actgactctg acgatcagtt gagaacacta | 300 |
| ggcgcaaacg ctggtcaatt ggtgaaggtt ttgccattgt ccgagagaaa ttaa | 354 |

```
<210> SEQ ID NO 16
<211> LENGTH: 1488
<212> TYPE: DNA
<213> ORGANISM: Artificial Sequence
<220> FEATURE:
<223> OTHER INFORMATION: Synthetic (aldH sequence)

<400> SEQUENCE: 16
```

| | |
|---|---:|
| atgaacttcc atcacctagc atattggcaa gacaaggcat tgtctttggc catcgaaaat | 60 |
| cgtttgttta tcaatggtga gtacaccgca gccgccgaga acgaaacatt cgaaactgtc | 120 |
| gatccagtta cccaagcacc attggctaag atcgcaagag gcaaatcagt ggacatagat | 180 |
| agagccatga gtgcagctag aggtgttttc aacgtggtg actggtcttt gtcaagtcca | 240 |
| gctaagagaa aagccgtctt gaacaagttg gctgacttga tggaagccca cgctgaagaa | 300 |
| ttagcttttgt tggaaaccctt ggacaccgga aaaccaatcc gtcattcttt gcgtgacgac | 360 |
| attcctggtg ctgctagggc tattagatgg tacgccgaag ctattgataa agtctacggt | 420 |
| gaggttgcta caactagttc ccatgagttg gcaatgatag tcagagagcc agtcggagtt | 480 |
| attgctgcta tcgtcccatg gaatttccca ttgttactta cctgttggaa gcttggtcca | 540 |
| gcattggccg ctggaaacag tgttatcttg aagccatccg aaaaatcccc attgagtgct | 600 |
| ataagattag caggtctagc taaggaagct ggtcttcctg acggtgtgct aaacgttgtt | 660 |
| acaggtttcg gtcacgaagc tggacaagcc ctatctaggc acaacgatat tgacgctatt | 720 |
| gccttcacag gttccactag aaccggtaag cagttactaa aggacgccgg tgactctaat | 780 |
| atgaagagag tctggttaga agctggtggt aaatccgcaa atattgtttt cgctgattgt | 840 |
| cctgatttac aacaggccgc ttctgctact gccgccggta tcttctacaa ccagggtcaa | 900 |
| gtttgcatcg caggtactag attgttgcta gaagaatcca ttgcagatga attcttagct | 960 |
| ctattgaagc aacaagctca aaactggcaa ccaggtcatc cattggaccc agctaccacc | 1020 |

```
atgggtactt tgatcgattg tgctcatgca gactctgttc actccttcat tagagaggga   1080
gaatcaaagg gtcaacttct tttggatggt agaaatgcag gcttggctgc cgctatcggt   1140
cctactatct tcgttgatgt tgacccaaac gcatccttgt caagagagga aattttcggc   1200
ccagtgttgg tggtcactag gtttacctct gaggaacaag cccttcagtt ggctaacgat   1260
tcacaatacg gcttaggtgc tgccgtctgg accagagatc tatctcgtgc ccacagaatg   1320
tctagaagat taaaggctgg ttccgtgttt gtgaacaact ataacgatgg tgacatgaca   1380
gttccttttg gtggttacaa gcagtctggt aacggcagag ataagtctct acacgccttg   1440
gaaaagttta ctgaattgaa gaccatctgg atctccttgg aggcttaa              1488

<210> SEQ ID NO 17
<211> LENGTH: 1446
<212> TYPE: DNA
<213> ORGANISM: Artificial Sequence
<220> FEATURE:
<223> OTHER INFORMATION: Synthetic (KGSadh)

<400> SEQUENCE: 17
atggccaacg ttacatacac tgatacacaa ttgctaatag acggtgagtg ggttgatgcc     60
gcatccggta agacaattga cgtcgtcaac ccagcaacag gtaagccaat cggtagagtt    120
gcacatgctg gtatcgccga cttggacaga gctttggcag ccgctcaaag tggtttcgaa    180
gcctggagaa aagttcctgc tcatgaacgt gctgccacta tgcgtaaagc tgctgcttta    240
gttcgtgaga gggccgatgc cattgctcaa cttatgactc aagaacaagg taagccttta    300
accgaggcaa gggttgaggt tttgtccgca gccgatatta ttgagtggtt cgctgacgaa    360
ggtagaagag tttatggtag aatcgtgcca ccacgtaacc taggcgctca gcaaactgtt    420
gtcaaggaac ctgtgggtcc agttgctgcc tttacccctt ggaacttccc agttaatcaa    480
gttgttagaa agttaagtgc cgcttttggc taccggttgca gttttttggt taaggctcca    540
gaagaaactc cagcttctcc tgcagctctt ttgagagcat ttgtcgacgc aggtgttcca    600
gctggcgtga ttggtttggt gtacggtgat ccagcagaaa tatcttcata tttgatccca    660
cacccagtca tcagaaaggt taccttcaca ggctcaaccc cagttggtaa acaattagct    720
tccttggctg gattgcatat gaagagagct accatggagt tgggtggaca cgctccagtc    780
atcgtggctg aagacgctga tgttgcttta gctgttaagg cagccggtgg cgcaaaattt    840
agaaatgctg gccaagtctg tatctctcct actcgtttct tggttcacaa ctctatcaga    900
gacgaattca ctagagcttt agtcaagcac gctgaaggcc taaaggtggg taacggtttg    960
gaagagggta ctactctagg tgctcttgcc aatccaagga gattgactgc tatggcttct   1020
gtcatcgata cgccaggaa ggtcggtgca tctattgaaa ccggtggaga gagaattggt   1080
tcagaaggta acttcttcgc accaaccgtg atcgcaaatg tgccactaga cgccgacgtc   1140
ttcaacaacg agccatttgg tccagtcgct gccattagag gtttcgataa attggaagaa   1200
gctatcgcag aagctaacag attgccattc ggattggctg gttacgcttt taccagatcc   1260
ttcgccaacg tgcacttatt gacccagaga ctagaagtgg gtatgttgtg gattaatcag   1320
ccagccaccc catggcctga atgcctttc ggtggtgtta aggattccgg ttacggttct   1380
gaaggtggac cagaagccct tgaaccatac ttggtcacca agtccgttac agtcatggcc   1440
gtctaa                                                             1446

<210> SEQ ID NO 18
```

```
<211> LENGTH: 24
<212> TYPE: DNA
<213> ORGANISM: Artificial Sequence
<220> FEATURE:
<223> OTHER INFORMATION: Synthetic (forward primer for dhaB1)

<400> SEQUENCE: 18
attgtggagt tggatggtaa gcgt                                          24

<210> SEQ ID NO 19
<211> LENGTH: 25
<212> TYPE: DNA
<213> ORGANISM: Artificial Sequence
<220> FEATURE:
<223> OTHER INFORMATION: Synthetic (reverse primer for dhaB1)

<400> SEQUENCE: 19
ccaagtcaag catggaggca atcaa                                         25

<210> SEQ ID NO 20
<211> LENGTH: 24
<212> TYPE: DNA
<213> ORGANISM: Artificial Sequence
<220> FEATURE:
<223> OTHER INFORMATION: Synthetic (forward primer for dhaB2)

<400> SEQUENCE: 20
ggagctaatc gctggtgttg aaga                                          24

<210> SEQ ID NO 21
<211> LENGTH: 26
<212> TYPE: DNA
<213> ORGANISM: Artificial Sequence
<220> FEATURE:
<223> OTHER INFORMATION: Synthetic (reverse primer for dhaB2)

<400> SEQUENCE: 21
ccaagtcgat atgtaaggtg acaggt                                        26

<210> SEQ ID NO 22
<211> LENGTH: 25
<212> TYPE: DNA
<213> ORGANISM: Artificial Sequence
<220> FEATURE:
<223> OTHER INFORMATION: Synthetic (forward primer for dhaB3)

<400> SEQUENCE: 22
ctatgagagt tcaggattac ccact                                         25

<210> SEQ ID NO 23
<211> LENGTH: 28
<212> TYPE: DNA
<213> ORGANISM: Artificial Sequence
<220> FEATURE:
<223> OTHER INFORMATION: Synthetic (reverse primer for dhaB3)

<400> SEQUENCE: 23
ccctttctta gcttatgtct ttgttggt                                      28

<210> SEQ ID NO 24
<211> LENGTH: 26
<212> TYPE: DNA
<213> ORGANISM: Artificial Sequence
<220> FEATURE:
<223> OTHER INFORMATION: Synthetic (forward primer for gdrA)

<400> SEQUENCE: 24
```

-continued

```
gagggttgga ttgttttgat cgatga                                          26

<210> SEQ ID NO 25
<211> LENGTH: 24
<212> TYPE: DNA
<213> ORGANISM: Artificial Sequence
<220> FEATURE:
<223> OTHER INFORMATION: Synthetic (reverse primer for gdrA)

<400> SEQUENCE: 25
cctctaatat ctctgacagg agca                                            24

<210> SEQ ID NO 26
<211> LENGTH: 23
<212> TYPE: DNA
<213> ORGANISM: Artificial Sequence
<220> FEATURE:
<223> OTHER INFORMATION: Synthetic (forward primer for gdrB)

<400> SEQUENCE: 26
tctttcccct ccaggtgtca ggt                                             23

<210> SEQ ID NO 27
<211> LENGTH: 24
<212> TYPE: DNA
<213> ORGANISM: Artificial Sequence
<220> FEATURE:
<223> OTHER INFORMATION: Synthetic (reverse primer for gdrB)

<400> SEQUENCE: 27
cggacaatgg caaaaccttc acca                                            24

<210> SEQ ID NO 28
<211> LENGTH: 23
<212> TYPE: DNA
<213> ORGANISM: Artificial Sequence
<220> FEATURE:
<223> OTHER INFORMATION: Synthetic (forward primer for aldH)

<400> SEQUENCE: 28
ctgacttgat ggaagcccac gct                                             23

<210> SEQ ID NO 29
<211> LENGTH: 25
<212> TYPE: DNA
<213> ORGANISM: Artificial Sequence
<220> FEATURE:
<223> OTHER INFORMATION: Synthetic (reverse primer for aldH)

<400> SEQUENCE: 29
ggaacctgtg aaggcaatag cgtca                                           25

<210> SEQ ID NO 30
<211> LENGTH: 27
<212> TYPE: DNA
<213> ORGANISM: Artificial Sequence
<220> FEATURE:
<223> OTHER INFORMATION: Synthetic (forward primer for KGSadh)

<400> SEQUENCE: 30
cgatgccatt gctcaactta tgactca                                         27

<210> SEQ ID NO 31
<211> LENGTH: 23
<212> TYPE: DNA
```

```
<213> ORGANISM: Artificial Sequence
<220> FEATURE:
<223> OTHER INFORMATION: Synthetic (reverse primer for KGSadh)

<400> SEQUENCE: 31
ccaaaccaat cacgccagct gga                                          23
```